US009532789B2

(12) United States Patent
Coope (10) Patent No.: US 9,532,789 B2
(45) Date of Patent: Jan. 3, 2017

(54) CANNULATED HAMMER DRILL ATTACHMENT (71) Applicant: BRITISH COLUMBIA CANCER AGENCY BRANCH, Vancouver (CA)

(72) Inventor: Robin John Noel Coope, Vancouver (CA)

(73) Assignee: BRITISH COLUMBIA CANCER AGENCY BRANCH, Vancouver (CA)

( * ) Notice: Subject to any disclaimer, the term of this patent is extended or adjusted under 35 U.S.C. 154(b) by 406 days.

(21) Appl. No.: 14/241,998

(22) PCT Filed: Nov. 14, 2012

(86) PCT No.: PCT/CA2012/050807
§ 371 (c)(1),
(2) Date: Feb. 28, 2014

(87) PCT Pub. No.: WO2014/075165
PCT Pub. Date: May 22, 2014

(65) Prior Publication Data
US 2015/0038970 A1    Feb. 5, 2015

(51) Int. Cl.
*A61B 17/16* (2006.01)
*A61B 17/84* (2006.01)
(Continued)

(52) U.S. Cl.
CPC ......... *A61B 17/1624* (2013.01); *A61B 17/162* (2013.01); *A61B 17/1637* (2013.01);
(Continued)

(58) Field of Classification Search
CPC .............. A61B 17/162; A61B 17/1624; A61B 17/1637; A61B 17/1662; A61B 17/844; Y10T 279/3406; Y10T 279/3412; Y10T 279/3418
(Continued)

(56) References Cited

U.S. PATENT DOCUMENTS 2,328,270 A    8/1943  Greenberg
2,724,573 A    11/1955 Lundquist
(Continued)

FOREIGN PATENT DOCUMENTS

BE    677249 A     8/1966
CA    1090169 A    11/1980
(Continued)

OTHER PUBLICATIONS

International Search Report and Written Opinion for International Patent Application No. PCT/CA2013/050870, mailed Feb. 20, 2014 (11 pages).
(Continued)

*Primary Examiner* — Anu Ramana
*Assistant Examiner* — Jessica Weiss
(74) *Attorney, Agent, or Firm* — Foley & Lardner LLP (57) ABSTRACT

A hammer drill attachment is provided for attachment to a bi-directional surgical drill. The hammer drill attachment is configured to provide a rotating output in a first direction of rotation when the drill is operated in its first direction of rotation, and the hammer drill attachment is configured to provide a hammering output when the drill is operated in its second direction of rotation.

19 Claims, 3 Drawing Sheets

(51) Int. Cl.
*A61B 17/86* (2006.01)
*B23B 45/00* (2006.01)

(52) U.S. Cl.
CPC ........ *A61B 17/1662* (2013.01); *A61B 17/844* (2013.01); *A61B 17/8625* (2013.01); *A61B 17/8685* (2013.01); *B23B 45/005* (2013.01)

(58) Field of Classification Search
USPC ....... 606/79–81, 85, 180; 279/143, 144, 145
See application file for complete search history.

(56) References Cited

U.S. PATENT DOCUMENTS

| | | | | |
|---|---|---|---|---|
| 3,371,725 A * | 3/1968 | Jansen | ................. | B25D 11/106 173/205 |
| 3,650,336 A * | 3/1972 | Koehler | ............... | B25D 16/003 173/110 |
| 3,774,699 A * | 11/1973 | Schmuck | ............. | B25D 16/006 173/109 |
| 4,098,351 A * | 7/1978 | Alessio | ................ | B25D 11/005 173/104 |
| 4,222,443 A * | 9/1980 | Chromy | ............... | B25D 11/125 173/14 |
| 4,450,919 A * | 5/1984 | Cousineau | ........... | B25D 17/005 173/29 |
| 4,489,792 A * | 12/1984 | Fahim | .................. | B25D 11/106 173/29 |
| 4,491,443 A * | 1/1985 | DeCaro | .................. | B25B 21/00 279/14 |
| 4,605,348 A * | 8/1986 | DeCaro | ................. | B25B 21/007 279/14 |
| 4,998,589 A * | 3/1991 | Wiesendanger | ........ | B23B 45/02 173/170 |
| 5,476,467 A * | 12/1995 | Benoist | ................. | A61B 17/92 606/100 |
| 5,741,253 A * | 4/1998 | Michelson | ............. | A61B 17/16 606/279 |
| 5,806,609 A * | 9/1998 | Stock | ................... | B25D 17/005 173/111 |
| 5,816,341 A * | 10/1998 | Bone | ...................... | B25D 16/00 173/114 |
| 5,899,425 A * | 5/1999 | Corey, Jr. | .............. | A61B 17/02 248/276.1 |
| 5,993,454 A * | 11/1999 | Longo | ................. | A61B 17/1624 606/80 |
| 5,996,454 A * | 12/1999 | Brinks, Jr. | ................. | B23B 5/02 82/1.11 |
| 6,044,918 A * | 4/2000 | Noser | .................... | B25D 16/00 173/176 |
| 6,110,174 A * | 8/2000 | Nichter | .............. | A61B 17/1697 606/103 |
| 6,286,611 B1 * | 9/2001 | Bone | ........................ | B25F 3/00 173/170 |
| 6,557,648 B2 * | 5/2003 | Ichijyou | ............... | B25D 16/006 173/201 |
| 6,684,964 B2 * | 2/2004 | Ha | ........................ | B25D 16/00 173/109 |
| 6,976,545 B2 * | 12/2005 | Greitmann | ........... | B25D 16/003 173/104 |
| 7,059,425 B2 * | 6/2006 | Ikuta | .................... | B25D 11/005 173/117 |
| 7,096,972 B2 | 8/2006 | Orozco, Jr. | | |
| 7,124,839 B2 * | 10/2006 | Furuta | .................. | B25B 21/026 173/104 |
| D537,940 S * | 3/2007 | Buttler | ........................ | D24/142 |
| 7,506,693 B2 * | 3/2009 | Stirm | .................. | B25D 11/005 173/104 |
| 7,513,317 B2 * | 4/2009 | Satou | .................... | B25D 17/24 173/109 |
| 2002/0056558 A1 * | 5/2002 | Bongers-Ambrosius | | B25D 11/12 173/201 |
| 2002/0170186 A1 * | 11/2002 | Sakaguchi | ............. | B23D 51/16 30/394 |
| 2004/0011565 A1 * | 1/2004 | Lyon | ...................... | E21B 10/36 175/296 |
| 2004/0050568 A1 * | 3/2004 | Orozco, Jr. | .......... | B25D 11/102 173/100 |
| 2005/0031424 A1 * | 2/2005 | Hernandez, Jr. | ...... | B23B 31/201 408/238 |
| 2005/0199407 A1 * | 9/2005 | Hermann | ............... | A61B 17/14 173/213 |
| 2006/0201688 A1 * | 9/2006 | Jenner | ..................... | B25B 21/00 173/48 |
| 2006/0237205 A1 * | 10/2006 | Sia | .......................... | B25B 21/00 173/48 |
| 2007/0056756 A1 * | 3/2007 | Chung | .................... | B25B 21/02 173/48 |
| 2008/0181740 A1 * | 7/2008 | Waitszies | ............ | B23B 31/1075 408/226 |
| 2010/0204613 A1 * | 8/2010 | Rollins | ........... | A61M 25/09041 600/585 |
| 2013/0161042 A1 * | 6/2013 | Blum | ....................... | B23Q 5/12 173/48 |
| 2013/0161043 A1 * | 6/2013 | Blum | ................... | B25D 16/006 173/48 |
| 2014/0182870 A1 * | 7/2014 | Herr | ..................... | B25D 11/104 173/94 |
| 2014/0309636 A1 * | 10/2014 | Meek | .................. | A61B 17/7208 606/62 |
| 2015/0038970 A1 * | 2/2015 | Coope | .................. | A61B 17/162 606/80 |

FOREIGN PATENT DOCUMENTS

| | | |
|---|---|---|
| CH | 445257 A | 10/1967 |
| CN | 2662839 Y | 12/2004 |
| DE | 1577998 C3 | 11/1974 |
| FR | 2361204 B1 | 4/1984 |
| GB | 1123452 A | 8/1968 |
| GB | 1 494 553 | 12/1977 |
| GB | 1584082 A | 2/1981 |
| IT | 1066884 B | 3/1985 |
| JP | S5334199 | 3/1978 |
| JP | S601150 B2 | 1/1985 |
| NL | 147356 B | 10/1975 |

OTHER PUBLICATIONS

International Search Report and Written Opinion for PCT/CA2012/050807 dated Nov. 12, 2012.

* cited by examiner

CANNULATED HAMMER DRILL ATTACHMENT

CROSS-REFERENCE TO RELATED APPLICATION

This application is a U.S. national stage filing under 35 U.S.C. §371 of International Application No. PCT/CA2012/050807, filed Nov. 14, 2012, entitled "CANNULATED HAMMER DRILL ATTACHMENT," the disclosure of which is incorporated by reference in its entirety.

BACKGROUND

The pelvis is a ring-like structure made up of three bones, the sacrum and two innominate bones that have three parts, the ilium, ischium, and pubis. The ring-like structure of the pelvic bones gives them great strength. Since the structure is ring-like, however, a fracture in one part of the structure will often be accompanied by another fracture or severe ligamentous injury at other points in the pelvic ring. Surgery is often required to repair the damage. Screws, bolts and metal plates facilitate the healing of the bones, and external fixators are common.

However, when external fixators are used, they may need to remain in place for as long as six to twelve weeks. Meticulous observation is required to spot signs of infection at the pin sites and note pins that are loosening and need to be replaced. Therefore, internal anchors are generally preferred. However, placing a plate on the bone requires a significant operation with resulting high blood loss. In some cases, a straight intramedullary screw may be placed along a curved path. While the screw is less invasive, because of the ring-shaped structure and curvature of the pelvic bones, the fixation may be inadequate because the straight screw cannot be implanted very far into a curved bone. This may result in inadequate fixation. Moreover, the screw must be relatively small in diameter to avoid extending through the bone. Surgically speaking, implanting a screw such that it extends from the bone can result in significant hazard to the patient because it may puncture or otherwise impinge upon important vascular and nervous structures.

Curved anchors and apparatus for forming curved holes for receiving the anchors can therefore be advantageous. Modified Kirschner wires having an angled distal tip may be driven into cancellous bone by a hammering action to form curved holes. Surgical drills provide only rotative motion in one or both directions of rotation and do not have a hammering capability. Therefore, in addition to a surgical drill, a hammering device or mechanism will also be needed during a fixation to drive the wire into the bone.

In order to simplify the tools, and/or the number of tools required by a surgeon for fixing bone fractures where curved fixation paths are required, there remains a need for an attachment device for a bi-directional rotary drill, such as a surgical drill, to convert the rotary drill to a hammer drill for driving modified drill wires into bone to produce curved bores for accepting bone anchors for fixing curved bone portions.

SUMMARY

Presently disclosed is a hammer drill attachment that enables a rotary drill to be used to provide a hammering action. The hammer drill attachment may be provided individually or as part of a drill kit that also includes a rotary drill, and the attachment may be usable in surgical procedures requiring a surgical drill implement to be hammered into bone.

In an embodiment, a hammer drill attachment is presented for a rotary drill that has an output member rotatable in a first direction and in a second direction opposite the first direction. The hammer drill attachment includes an input shaft configured for receiving rotary motion from an output member of a rotary drill in each of the first direction and the second direction, an output shaft configured for outputting rotary motion or pulsed axial percussions, and a transmission connecting the input shaft with the output shaft. The transmission is configured to transmit rotary motion from the input shaft to the output shaft during rotation of the input shaft in the first direction of rotation and to convert rotary motion of the input shaft to pulsed axial percussions of the output shaft during rotation of the input shaft in the second direction of rotation.

In an additional embodiment, a surgical drill kit is presented. The drill kit includes a rotary cannulated drill having an output member with an axial bore therein and rotatable in a first direction and a second direction opposite the first direction, and a cannulated hammer drill attachment configured to be fixedly attached to the drill. The hammer drill attachment includes a housing that has an attachment portion for non-rotationally connecting the housing to the drill, a cannulated input shaft configured to receive rotary motion from the output member of the drill, the input shaft comprising an axial bore, a cannulated output shaft axially aligned with the input shaft and configured to output rotary motion or pulsed axial percussions, the output shaft comprising an axial bore, and a transmission connecting the input shaft with the output shaft. The transmission including a transmission element configured to transmit rotary motion from the input shaft to the output shaft during rotation of the input shaft in a first direction of rotation and to convert rotary motion of the input shaft to pulsed axial percussions of the output shaft during rotation of the input shaft in a second direction of rotation.

In a further embodiment, a method for surgically drilling is presented. The method includes connecting a cannulated hammer drill attachment to a cannulated surgical drill. The surgical drill includes an output member rotatable in a first direction and in a second direction opposite the first direction, and the output member defines an axial cannula extending therethrough. The cannulated hammer drill attachment includes a cannulated input shaft configured for receiving rotary motion from the output member and rotating in each of the first direction and the second direction, a cannulated output shaft in axial alignment with the input shaft and configured to output rotary motion or pulsed axial percussions, and a transmission connecting the input shaft with the output shaft. The transmission is configured to transmit rotary motion from the input shaft to the output shaft during rotation of the input shaft in the first direction of rotation, and convert rotary motion of the input shaft to pulsed axial percussions of the output shaft during rotation of the input shaft in the second direction of rotation. The method also includes inserting a surgical drill implement through cannula of the drill output member and the input and output shafts of the hammer drill attachment, fixedly retaining the drill implement with the output shaft to receive rotary motion or pulsed axial percussions from the output shaft, and operating the drill. The drill may be operated in the first direction of rotation to rotate the input shaft in the first direction of rotation and output rotary motion to the output shaft and retained drill implement to rotatably drill the implement into the bone, or the second direction of rotation to rotate the input shaft in the second direction of rotation and output pulsed axial percussions to the output shaft and retained drill implement to hammer drive the implement into the bone.

DETAILED DESCRIPTION

The pelvic bones exhibit many areas of curvature. Fractures of the pelvic bones therefore may often require curved intramedullary anchors to fix the bones. However, to use curved anchors, the holes for receipt of the anchors must also be curved and typical drill arrangements do not allow for the formation of curved holes. Curved holes may be created by using a bent and sharpened tip on the end of a piece of flexible wire, and advancing the wire into the bone by a hammering action. The hammering action may be provided by a cannulated hammer drill system as described with reference to FIGS. 1-3, and the wire may have a configuration as depicted in FIG. 5.

Figure 5:
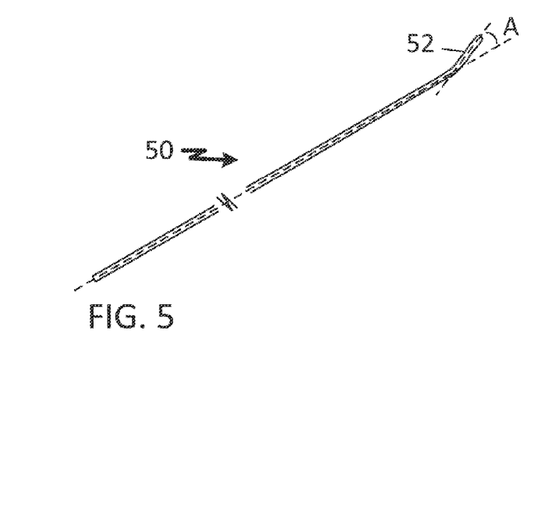
FIG. 5 depicts a Kirschner wire having a bent tip for producing curved holes in bone according to an embodiment.

Flexible drill wires, such as the wire 50 depicted in FIG. 5, which may be used to produce curved holes, may be formed from materials such as nitinol (nickel titanium) or spring tempered stainless steel, for example. Depending on the diameter desired for the hole, the wire 50 may have a diameter from about 0.5 mm to about 5 mm. In embodiments, the wire 50 may have a diameter of about 0.5 mm, about 0.75 mm, about 1.0 mm, about 1.25 mm, about 1.5 mm, about 1.75 mm, about 2.0 mm, about 2.5 mm, about 3.0 mm, about 3.5 mm, about 4.0 mm, about 5.0 mm, or any diameter between any two of the listed values. To enable the wire 50 to be advanced in a non-linear direction with respect to the longitudinal axis of the wire, the tip 52 of the wire may be bent at an angle from the longitudinal axis. The angled tip 52 may have a length of about 5 mm to about 12 mm extending from the end. In embodiments, the angled tip 52 may have a length of about 5 mm, about 6 mm, about 7 mm, about 8 mm, about 9 mm, about 10 mm, about 11 mm, about 12 mm, or any length between any of the listed values. The angled tip 52 may be bent from the longitudinal axis at an angle A of about 25° to about 35°. In embodiments, the angled tip 52 may be disposed at an angle A of about 25°, about 26°, about 27°, about 28°, about 29°, about 30°, about 31°, about 32°, about 33°, about 34°, about 35°, or any angle between any of the listed values. As an example, a drill wire 50 may be on the order of about 1.5 mm in diameter, and may include a bent tip 52 of about 10 mm in length at an angle A of about 30°.

A drill wire 50 may be advanced within the soft cancellous bone inside the pelvis by means of a hammering action. The bent tip 52 will cause the wire 50 to turn, or be directed off axis in the direction of the angled tip as the wire is advanced. If the wire 50 is able to be rotated to turn the tip 52 in any arbitrary orientation, the overall direction of the wire can be made to bend in the direction which is required. Straight paths may be approximated by alternately turning the tip 52 at 180° offsets and producing several short curved paths in opposing directions. A fluoroscope may be used to continuously monitor the position of the drill in the bone, and allow adjustments to be made as the hole is being formed. The process of producing curved holes within the pelvis is aided by the outer structure of hard cortical bone which can partially guide the wire within the softer cancellous bone of the pelvis.

Figure 1:
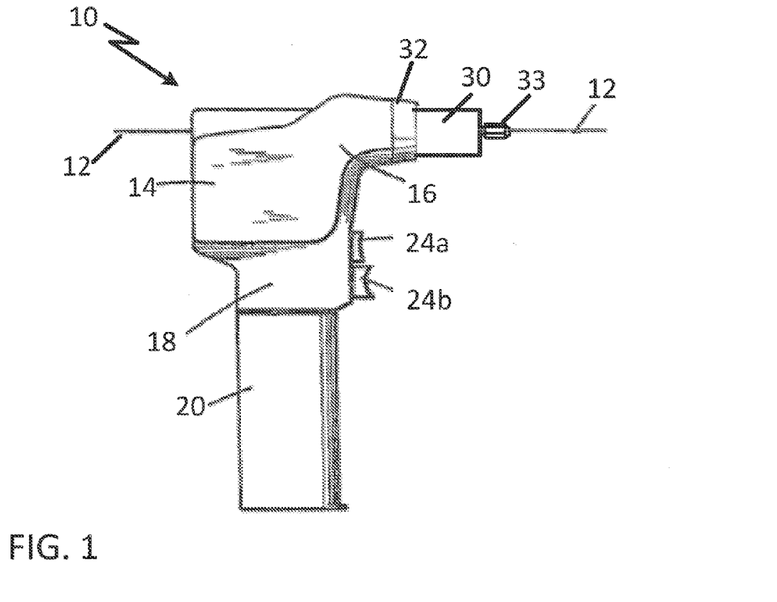
FIG. 1 depicts a cannulated surgical drill according to an embodiment.

To produce the hammering action needed to drive the wire drill 50 into bone, a hammer drill attachment 30 may be attached to a standard bi-directional surgical drill 10 as shown in FIG. 1.

With reference to FIG. 1, there is illustrated a surgical drill 10 which may be a cannulated drill configured for accepting a Kirschner wire 12 (also referred to as a "K-wire" or "K-pin") through the cannula thereof. The drill 10 may be a bi-directional drill, while use of a unidirectional drill may also be contemplated. Some examples of surgical drills are the MPower® and PowerPro® devices manufactured by ConMed Linvatec of Largo Fla.

With the inclusion of a cannulated hammer-drill attachment 30, discussed in more detail with reference to FIGS. 2 and 3, a surgical drill 10 may be adapted to drive the Kirschner pin 12 into the bone. If the pins 12 are configured as discussed with reference to wire 50 of FIG. 5, curved hole paths may be formed in the bone. Hammer-drill attachment 30 may be attached to the drill body by means of an attachment device 32. The drill 10 may also be used with other types of attachments, and some examples of additional attachments which may be used include, but are not limited to, keyless chucks, quick-connect drill attachments, reamers, sagittal saws, and reciprocating saws.

While a cannulated drill may have a variety of configurations, in general, a drill 10 may include a motor housing 14, a gear housing 16 forwardly thereof, a depending pistol-grip handle 18, and a removable battery pack 20 which may form a part of the pistol-grip handle. The handle 18 may be ergonomically designed and include a pair of triggers 24a, 24b projecting forwardly of the pistol-grip handle. In an embodiment, trigger 24a may provide a first, or forward direction of rotation, and trigger 24b may provide a second, or reverse direction of rotation. The triggers 24a, 24b may be variable speed triggers that provide control of the speed of rotation. The hammer-drill attachment 30 may include a rotary connection member, such as a collet 33, for engaging the K-wire 12 and rotating the K-wire with the rotation of the drill motor. During usage of such a configuration, a surgeon may control the operation of the drill (speed, direction of rotation, insertion or withdrawal) with one hand.

As depicted in FIG. 1, surgical drills, including cannulated surgical drills, may have two separate buttons to control direction, unlike conventional drills which generally have one trigger to run the drill and a separate bi-stable switch to control direction. The hammer drill attachment 30 of FIGS. 2 and 3 includes a clutch 32, which may be a unidirectional bearing, and which exploits the bi-directional design. This clutch bearing 32 allows the attachment to provide free rotation in a first direction of rotation, while inhibiting rotation in the opposite, second direction and allowing the rotation in the second direction to be converted into a hammering motion. The attachment 30 may have a housing 40 that retains the attachment parts and provides an attachment portion 42 to engage with and fixedly retain the housing on the drill to prohibit rotation of the housing upon operation of the drill.

Attachment 30 includes an input shaft 34 configured to receive rotary motion from an output member (not shown) of a rotary drill in each of the first direction of rotation and the second direction of rotation of the drill. Input shaft 34 rotates freely in both directions. Attachment 30 also includes an output shaft 35 configured for outputting rotary motion or pulsed axial percussions, and a transmission arrangement 31 connecting the input shaft with the output shaft. In an embodiment as depicted in FIGS. 2 and 3, the input shaft 34 and output shaft 35 are in axial alignment and are cannulated for receipt of a K-wire therethrough, and may therefore be used with cannulated surgical drills.

The transmission arrangement 31 is configured to transmit rotary motion from the input shaft 34 to the output shaft 35 during rotation of the input shaft in the first direction of rotation, and is also configured to convert rotary motion of the input shaft to pulsed axial percussions of the output shaft during rotation of the input shaft in the second direction of rotation. In an embodiment, the transmission arrangement 31 may include a first transmission member 36 disposed in conjunction with the input shaft 34 to receive corresponding rotary motion from the input shaft during rotation of the input shaft in each of the first direction of rotation and the second direction of rotation. The transmission arrangement 31 may also include a second transmission member 37 disposed in conjunction with the first transmission member 36 and the output shaft 35 to transfer the rotary motion of the first transmission member to the output shaft during rotation of the input shaft in the first direction of rotation, and convert the rotary motion of the first transmission member to pulsed axial percussions and transfer the pulsed axial percussions to the output shaft during rotation of the input shaft in the second direction of rotation.

The input shaft 34 has a first end configured to be connected to an output member of a drill and a second end spaced apart from the first end and disposed within the housing 40. The output shaft 35 has a first end disposed within the housing 40 adjacent the second end of the input shaft and a second end spaced apart from the first end. The first transmission member 36 may be fixedly attached on the second end of the input shaft 34 for rotation of the first transmission member with the input shaft, and the second transmission member 37 may be fixedly attached on the first end of the output shaft 35 for movement of the output shaft with the second transmission member. In the embodiment as depicted in FIGS. 2 and 3, the first transmission member is configured as a saw-tooth disc 36, and the second transmission member is configured as a saw-tooth disc 37.

In an embodiment, at least one of the first transmission member and the second transmission member (corresponding with either 36 or 37 in the embodiment of FIG. 3) may be a disc-shaped member having a surface disposed towards the other of the first transmission member and the second transmission member. As shown in FIG. 3, the surface of the disc shaped member 36 or 37 may have a plurality of teeth disposed annularly about a central axis. As depicted in the representation presented by FIG. 4, the teeth may have a right-triangular cross-section in the annular direction with a face portion disposed at an angle to the surface and a leg portion disposed axially to the surface.

Figure 3:
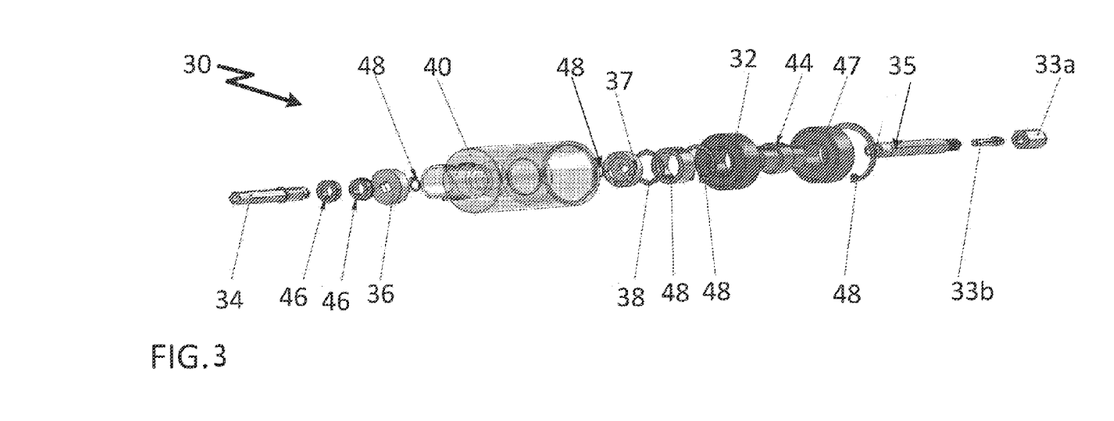
FIG. 3 depicts an exploded perspective view of the cannulated hammer drill attachment of FIG. 2 according to an embodiment.
Figure 4:
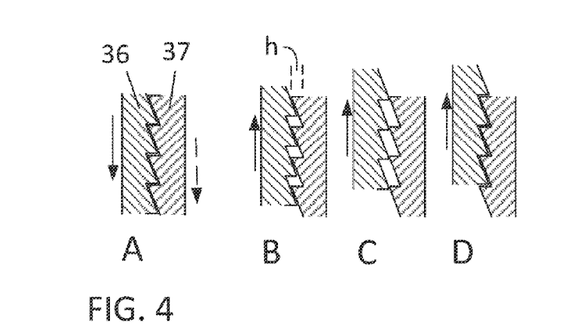
FIG. 4 illustrates the engagement between transmission plates of a cannulated hammer drill according to an embodiment.

In an embodiment, the other of the first transmission member and the second transmission member (corresponding with the other of either 36 or 37 in the embodiment of FIG. 3) may be configured as an engagement device having at least one projection that is configured to engage with the leg portions of the teeth during rotation of the input shaft 34 in the first direction of rotation to rotate the second transmission member with the first transmission member, and glidingly move over the face portions of the teeth during rotation of the input shaft in the second direction of rotation to axially displace the output shaft 35 by an amount which is substantially the height of the teeth from the surface of the disc (see h in FIG. 4). A biasing member, which may be configured as a wave washer, such as wave washer 38 in FIG. 3, may be disposed to provide biased engagement between the teeth of the one transmission member and the at least one projection of the other transmission member.

Figure 2:
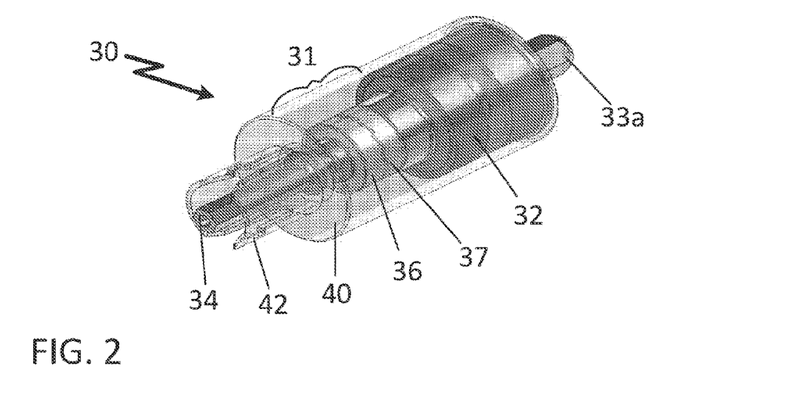
FIG. 2 depicts a perspective view of a cannulated hammer drill attachment according to an embodiment.

In the embodiment as depicted in FIGS. 2 and 3, both of the first and second transmission members 36, 37 may be saw-toothed disc members with a plurality of teeth disposed annularly about a central axis. As represented in FIG. 4, the teeth on the disc members 36, 37 may be complementary to one another. Upon movement of the disc member 36 in a first direction of rotation as represented by panel A of FIG. 4, the leg portions of the teeth of the first disc member 36 engage with the leg portions of the teeth of the second disc member 37 and rotate the second disc member with the first disc member. However, as represented by panels B-D of FIG. 4, upon rotation of the first disc member 36 in the opposite direction, since disc member 37 is prevented from rotating in the opposite direction by the unidirectional bearing 32, the teeth of the first disc member slide over the face portions of the teeth of the second disc member to axially displace the second disc member by an amount h corresponding to the height of the teeth. After the teeth pass over one another, the discs snap back together (panel D) and an axial hammering movement is created.

This axial displacement results in an axial displacement of the output shaft 35, and any surgical implement connected with the output shaft via the collet 33. In some designations, the term 'chuck' may be used interchangeably with the term 'collet.' A collet 33 may include an engaging member 33b through which the article to be retained is held, and an internally threaded cap 33a that may be threadable onto the end of the shaft 35 to compress the engaging member around the implement to be retained.

A unidirectional bearing 32 prohibits rotation of the second disc member 37 and shaft 35 in the second direction. A bushing 44 may be provided to allow for axial movement of the shaft 35 within the unidirectional bearing 32. Additional bearings 46, 47 may be provided as needed to guide rotation of the shafts 34, 35, and retaining rings 48 may be used to hold the various components in place within the housing and on the shafts. A spacer ring 49 may also be included to provide a bearing surface for the wave washer 38.

A hammer drill attachment 30 may be packaged and sold individually as an accessory for rotary drills, or alternatively may be included in a pre-packaged kit. A kit may include a drill, such as drill 10 of FIG. 1, as well as assorted attachment devices, such as the hammer drill attachment 30 or any of the previously mentioned attachments including keyless chucks, quick-connect drill attachments, reamers, sagittal saws, and reciprocating saws.

EXAMPLE 1

Cannulated Hammer Drill Attachment

A hammer drill attachment 30 as shown in FIG. 2 and constructed as shown in the exploded view of FIG. 3 has a housing 40 that has an attachment portion 42 which is configured to be attached to a drill, such as drill 10 of FIG. 1. The attachment portion 42 may be configured as needed to enable the attachment 30 to be used for various models of drills 10. The attachment 30 has an input shaft 34 that engages with the drive of the drill and an output shaft 35 coaxial with the input shaft. A collet 33 is provided on the output shaft 35 to connect the output shaft with a drill wire. The shafts are cannulated for passage of a surgical drill wire therethrough to enable the attachment to be used with cannulated surgical drills. The attachment 30 is configured with a transmission arrangement that allows the output shaft 35 to rotate only in one direction upon rotation of the input shaft 34 in a first direction. Upon rotation of the input shaft 34 in the opposite direction, the transmission converts the rotation into a hammering action to produce a hammering action at the output shaft 35.

EXAMPLE 2

Surgical Drill Kit

A surgical drill kit may include a cannulated surgical drill such as drill 10 of FIG. 1. A cannulated hammer drill attachment 30 may be included as part of the kit, and various other optional attachment devices may also be included, such as keyless chucks, quick-connect drill attachments, reamers, sagittal saws, and reciprocating saws. In addition to any attachment devices, device accessories may also be included such as rechargeable batteries, saw blades, and drill bits, and may include drill wires, such as various gauges of Kirschner wires 12 of FIG. 1 and/or a drill wire 50 of FIG. 5. Kits may be sold as pre-packaged assortments of contents, or may be custom ordered to create a kit that meets the needs of a particular surgeon.

EXAMPLE 3

Surgery for Repair of Pelvic Fractures

An incision of approximately 3 cm will be made in a patient at a location from which the surgeon wishes to approach the broken bone. Upon exposing the bone, the surgeon will drill a first hole through the outer cortical bone using a surgical drill (such as drill 10 of FIG. 1) equipped with a standard drill chuck and an appropriate drill bit. The hole will be drilled using the forward drill rotation button to drill into the bone. The standard drill chuck will be removed and a cannulated hammer drill attachment 30 will be affixed to the drill via the attachment portion 42 of the housing 40. A K-wire (50 of FIG. 5) having a diameter of about 1.5 mm and a sharpened tip of about 10 mm disposed at an angle A of about 30° from the axis of the wire will then be inserted through the cannula of the drill and hammer drill attachment.

A fluoroscope will be used to track progress of the wire through the bone. The bent and sharpened tip will be inserted into the drilled hole and directed in a first direction in which it is desired to form a curved hole. The surgeon will press the reverse rotation button and produce a hammering output to drive the tip and wire into the cancellous bone to divert the hole in the first direction. Upon reaching a satisfactory extent of curvature of the hole in the desired first direction and wishing to then proceed in a straight path, the surgeon will rotate the tip 180° from the first direction and hammer drive the wire into the bone approximately another 0.5 cm to 1 cm. The tip will again be rotated 180° back to its original direction and advance by hammering another approximately 0.5 cm to 1 cm. This back and forth reversal of direction will be repeated until an approximately straight hole of a desired length is achieved. Further curvature, and/or straight path segments will be made as needed in the manner as discussed above to produce a bore within the bone in a desired position for receipt of a fixation anchor therein.

Figure 6A:
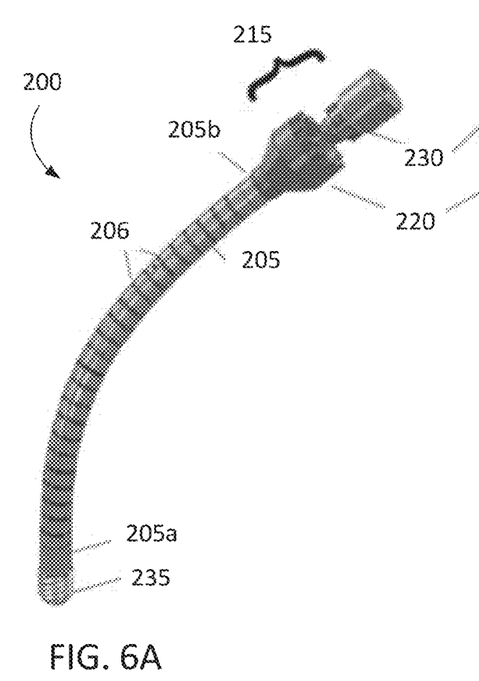
FIG. 6A depicts an exemplary device for fixing a bone according to an embodiment.
Figure 6B:
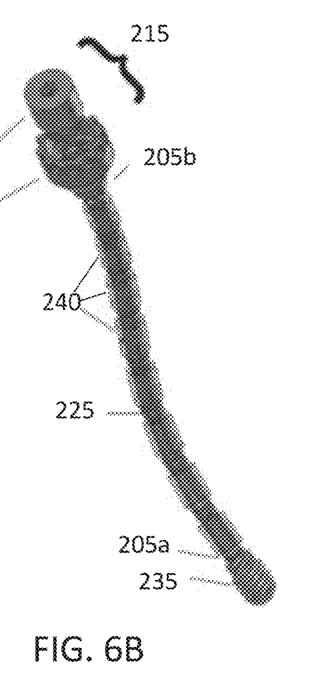
FIG. 6B depicts interior portions of the exemplary device of FIG. 2A according to an embodiment.

The K-wire will be left in place, and the curved bore established by the K-wire will be enlarged to about 10 mm diameter by placing a cannulated reamer having a flexible cannulated drive shaft on the K-wire. With visualization provided by the fluoroscope, the reamer will be advanced along the K-wire to approximately the bent tip of the wire. The reamer and wire will be withdrawn leaving an open 10 mm diameter bore through the bone. A fixation device, such as the device 200 as illustrated in FIGS. 6A and 6B, having a corresponding diameter will be inserted into the bore. The device 200 may include a flexible tube 205, a stiffening mechanism 210, an actuator 215, and a threaded screw anchor portion 235.

The anchor portion 235 will be threaded into the bone at the end of the bore to anchor the device 200 in place. The flexible tube 205 may have a distal end 205a and a proximal end 205b. The flexible tube 205 may include a plurality of slits, such as 206, in an outer housing configured to allow the flexible tube to flex. In an embodiment, the flexible tube 205 may comprise stainless steel and/or nitinol. The stiffening mechanism 210 may be located within the flexible tube 205 and may be configured to cause the flexible tube to become rigid. In an embodiment, the stiffening mechanism 210 may include a plurality of expansion sleeves 240 abutting one another at joints 225. The sleeves 240 will be actuated by rotation of the actuator 215 to expand the sleeves to abut an interior surface of the flexible tube 205 thereby causing the tube to become rigid. A locking assembly 230 will then be engaged with the cap 220 to retain the system in a rigid locked configuration to hold the bone fragments in place.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A cannulated hammer drill attachment for a cannulated rotary drill having an output member rotatable in a first direction and in a second direction opposite the first direction, wherein the hammer drill attachment comprises: an input shaft configured to receive rotary motion from an output member of the rotary drill in each of the first direction and the second direction; an output shaft configured to output rotary motion or pulsed axial percussions; and a transmission connecting the input shaft with the output shaft, the transmission comprising: a first transmission member disposed in conjunction with the input shaft to receive corresponding rotary motion from the input shaft during rotation of the input shaft in each of the first direction of rotation and the second direction of rotation; and a second transmission member disposed in conjunction with the first transmission member and the output shaft, the second transmission member being configured to: during rotation of the input shaft in the first direction of rotation, transfer the rotary motion of the first transmission member to the output shaft, and during rotation of the input shaft in the second direction of rotation, convert the rotary motion of the first transmission member to pulsed axial percussions and transfer the pulsed axial percussions to the output shaft.

2. The cannulated hammer drill attachment of claim 1, further comprising a device to prohibit rotary motion of the output shaft in the second direction of rotation during rotation of the input shaft in the second direction of rotation.

3. The cannulated hammer drill attachment of claim 1, wherein:
the input shaft has a first end configured to be connected to an output member of a drill and a second end spaced apart from the first end;
the output shaft is in axial alignment with the input shaft and has a first end disposed adjacent the second end of the input shaft and a second end spaced apart from the first end;
the first transmission member is fixedly attached on the second end of the input shaft to rotate the first transmission member with the input shaft; and
the second transmission member is fixedly attached on the first end of the output shaft to move the output shaft with the second transmission member.

4. The cannulated hammer drill attachment of claim 3, wherein:
the first transmission member comprises a first disc-shaped member disposed on the second end of the input shaft, the first disc-shaped member comprising:
a surface disposed towards the first end of the output shaft and having a peripheral edge, and
a plurality of teeth disposed on the surface adjacent at least the peripheral edge, wherein the teeth have a right-triangular cross-section in the peripheral direction with a face portion disposed at an angle to the surface and a leg portion disposed axially to the surface;
the second transmission member comprises a second disc-shaped member disposed on the first end of the output shaft, the second disc-shaped member comprising:
a surface disposed towards the surface of the first transmission member and having a peripheral edge, and
a plurality of teeth disposed on the surface adjacent at least the peripheral edge, wherein the teeth have a right-triangular cross-section in the peripheral direction with a face portion disposed at an angle to the surface and a leg portion disposed axially to the surface; and
the teeth on the surface of the first disc-shaped member are complementary to the teeth on the surface of the second disc-shaped member, wherein:
the leg portions of the teeth of the first disc-shaped member engage with the leg portions of the teeth of the second disc-shaped member during rotation of the input shaft in the first direction of rotation to rotate the second transmission member with the first transmission member, and
the face portions of the teeth of the first disc-shaped member slide over the face portions of the teeth of the second disc-shaped member during rotation of the input shaft in the second direction of rotation to axially displace the second transmission member with respect to the first transmission member to axially displace the output shaft.

5. The cannulated hammer drill attachment of claim 4, further comprising a biasing member to provide biased engagement between the teeth on the surface of the first disc-shaped member and the teeth on the surface of the second disc-shaped member.

6. The cannulated hammer drill attachment of claim 4, further comprising a housing, wherein:
the input shaft and first transmission member are axially fixed within the housing;
the output shaft and second transmission member are axially displaceable within the housing; and
the housing comprises a portion to engage with a body portion of a rotary drill to prohibit rotation of the attachment with respect to the drill.

7. The cannulated hammer drill attachment of claim 4, further comprising:
a housing;
at least one first bearing disposed around the input shaft between the input shaft and the housing; and
at least one second bearing disposed around the output shaft between the output shaft and the housing, and configured to permit rotation of the output shaft in the first direction and prohibit rotation of the output shaft in the second direction of rotation.

8. The cannulated hammer drill attachment of claim 1, wherein:
at least one of the first transmission member and the second transmission member comprises a disc-shaped member having a surface disposed towards the other of the first transmission member and the second transmission member, the surface comprising a plurality of teeth disposed annularly about an axis defined by the input shaft and the output shaft, wherein the teeth have a right-triangular cross-section in the annular direction with a face portion disposed at an angle to the surface and a leg portion disposed axially to the surface;
the other of the first transmission member and the second transmission member comprises at least one projection configured to:
engage with the leg portions of the teeth during rotation of the input shaft in the first direction of rotation to rotate the second transmission member with the first transmission member, and
glidingly move over the face portions of the teeth during rotation of the input shaft in the second direction of rotation to axially displace the output shaft; and
the attachment further comprises a biasing member to provide biased engagement between the teeth and the at least one projection.

9. The cannulated hammer drill attachment of claim 1, wherein the attachment is cannulated for use with a cannulated surgical drill.

10. The cannulated hammer drill attachment of claim 1, wherein the input shaft and output shaft are axially aligned and comprise an axial cannulation extending therethrough and configured to receive an elongated surgical implement therethrough.

11. A surgical drill kit comprising: a rotary cannulated drill having an output member rotatable in a first direction and in a second direction opposite the first direction, the output member having an axial bore therein; and a cannulated hammer drill attachment configured to be fixedly attached to the drill, the attachment comprising: a housing comprising an attachment portion to non-rotationally connect the housing to the drill; a cannulated input shaft configured to receive rotary motion from the output member of the drill, the input shaft comprising an axial bore; a cannulated output shaft axially aligned with the input shaft and configured to output rotary motion or pulsed axial percussions, the output shaft comprising an axial bore; and a transmission connecting the input shaft with the output shaft, the transmission comprising: a first transmission member disposed in conjunction with the input shaft to receive corresponding rotary motion from the input shaft during rotation of the input shaft in each of the first direction of rotation and the second direction of rotation; and a second transmission member disposed in conjunction with the first transmission member and the output shaft, the second transmission member being configured to: during rotation of the input shaft in the first direction of rotation, transfer the rotary motion of the first transmission member to the output shaft, and during rotation of the input shaft in the second direction of rotation, convert the rotary motion of the first transmission member to pulsed axial percussions and transfer the pulsed axial percussions to the output shaft.

12. The kit of claim 11, further including at least one surgical implement adapted to be inserted through the axial bores of the output member, the input shaft and the output shaft, wherein the at least one surgical implement is adapted to be rotatably driven or axially pulsed by the output shaft, wherein the output shaft comprises a device to fixedly connect the output shaft with the surgical implement to rotate or axial pulse the surgical implement with the output shaft.

13. The kit of claim 11, wherein:
the input shaft has a first end configured to be connected to the output member of the drill, and a second end spaced apart from the first end;
the output shaft has a first end disposed adjacent the second end of the input shaft, and a second end spaced apart from the first end;
the first transmission member is fixedly attached on the second end of the input shaft to rotate the first transmission member with the input shaft; and
the second transmission member is fixedly attached on the first end of the output shaft to move the output shaft with the second transmission member.

14. The kit of claim 13, wherein:
the first transmission member comprises a first disc-shaped member disposed on the second end of the input shaft, the first disc-shaped member comprising:
a surface disposed towards the first end of the output shaft and having a peripheral edge, and
a plurality of teeth disposed on the surface adjacent at least the peripheral edge, wherein the teeth have a right-triangular cross-section in the peripheral direction with a face portion disposed at an angle to the surface and a leg portion disposed axially to the surface;
the second transmission member comprises a second disc-shaped member disposed on the first end of the output shaft, the second disc-shaped member comprising:
a surface disposed towards the surface of the first transmission member and having a peripheral edge, and
a plurality of teeth disposed on the surface adjacent at least the peripheral edge, wherein the teeth have a right-triangular cross-section in the peripheral direction with a face portion disposed at an angle to the surface and a leg portion disposed axially to the surface; and
the teeth on the surface of the first disc-shaped member are complementary to the teeth on the surface of the second disc-shaped member, wherein:
the leg portions of the teeth of the first disc-shaped member engage with the leg portions of the teeth of the second disc-shaped member during rotation of the input shaft in the first direction of rotation to rotate the second transmission member with the first transmission member, and
the face portions of the teeth of the first disc-shaped member slide over the face portions of the teeth of the second disc-shaped member during rotation of the input shaft in the second direction of rotation to axially displace the second transmission member with respect to the first transmission member to axially displace the output shaft.

15. The kit of claim 11, wherein the hammer drill attachment further comprises:
at least one first bearing disposed around the input shaft between the input shaft and the housing; and
at least one second bearing disposed around the output shaft between the output shaft and the housing, and configured to permit rotation of the output shaft in the first direction and prohibit rotation of the output shaft in the second direction of rotation.

16. A method for surgically drilling in bone, the method comprising: connecting a cannulated hammer drill attachment to a cannulated surgical drill, wherein: the surgical drill comprises an output member rotatable in a first direction and in a second direction opposite the first direction, the output member defining an axial bore extending therethrough, and the cannulated hammer drill attachment comprises: a cannulated input shaft configured to receive rotary motion from the output member and rotate in each of the first direction and the second direction, a cannulated output shaft in axial alignment with the input shaft and configured to output rotary motion or pulsed axial percussions, and a transmission connecting the input shaft with the output shaft, the transmission comprising: a first transmission member disposed in conjunction with the input shaft, and a second transmission member disposed in conjunction with the first transmission member and the output shaft, wherein rotary motion from the input shaft is transmitted to the output shaft during rotation of the input shaft in the first direction of rotation, and rotary motion of the input shaft is converted to pulsed axial percussions of the output shaft during rotation of the input shaft in the second direction of rotation;
inserting a surgical drill implement through the axial bore of the drill output member and the cannulated input and output shafts of the hammer drill attachment; fixedly retaining the drill implement with the output shaft to receive rotary motion or pulsed axial percussions from the output shaft; and operating the drill in: the first direction of rotation to rotate the input shaft in the first direction of rotation and output rotary motion to the output shaft and retained drill implement to rotatably drill the implement into the bone, and the second direction of rotation to rotate the input shaft in the second direction of rotation and output pulsed axial percussions to the output shaft and retained drill implement to hammer drive the implement into the bone.

17. The method of claim 16, wherein operating the drill in the first direction of rotation and the second direction of rotation advances the drill implement into the bone along with movement of the drill and attachment toward the bone, and after advancing the drill implement into the bone, the method further comprises:

loosening the drill implement with respect to the output shaft;

sliding the drill and attachment axially along the drill implement in a direction away from the bone;

fixedly retaining the drill implement with the output shaft; and     operating the drill in:

the first direction of rotation to rotate the input shaft in the first direction of rotation and output rotary motion to the output shaft and retained drill implement to rotatably drill the implement into the bone, and         the second direction of rotation to rotate the input shaft in the second direction of rotation and output pulsed axial percussions to the output shaft and retained drill implement to hammer drive the implement into the bone.

18. The method of claim 16, wherein the drill implement comprises a drill wire, the drill wire comprising a distal tip end configured to be inserted into the bone, and operating the drill in the first direction, rotatably drilling the distal tip end through harder bone, and operating the drill in the second direction, axially hammering the distal tip end through softer bone.

19. The method of claim 18, wherein the distal tip end is disposed at an angle with respect to a longitudinal axis of the drill wire, and     for a curved path of the drill wire, operating in the second direction comprises turning the bent tip in a desired direction and axially hammering the drill wire to direct the drill wire in a direction of the bent tip to provide a curved path of the drill wire; and     for a substantially straight path of the drill wire, operating in the second direction comprises turning the bent tip in a first direction, axially hammering the drill wire, turning the bent tip in a second direction 180° from the first direction, axially hammering the drill wire, and intervally repeating the hammering in the first and second directions to provide a substantially straight path of the drill wire.

* * * * *